(12) United States Patent
Larsen

(10) Patent No.: US 11,083,617 B2
(45) Date of Patent: Aug. 10, 2021

(54) OSTOMY DEVICE

(71) Applicant: MULTI-LOCK ApS, Haderslev (DK)

(72) Inventor: Martin Larsen, Haderslev (DK)

(73) Assignee: MULTI-LOCK APS, Haderslev (DK)

( * ) Notice: Subject to any disclaimer, the term of this patent is extended or adjusted under 35 U.S.C. 154(b) by 710 days.

(21) Appl. No.: 15/706,003

(22) Filed: Sep. 15, 2017

(65) Prior Publication Data
US 2018/0000628 A1 Jan. 4, 2018

Related U.S. Application Data

(63) Continuation of application No. PCT/DK2016/050079, filed on Mar. 18, 2016.

(30) Foreign Application Priority Data

Mar. 18, 2015 (DK) .................................. 201500164

(51) Int. Cl.
A61F 5/441 (2006.01)
A61F 5/448 (2006.01)
A61F 5/44 (2006.01)
A61F 5/445 (2006.01)

(52) U.S. Cl.
CPC .............. *A61F 5/441* (2013.01); *A61F 5/445* (2013.01); *A61F 5/448* (2013.01); *A61F 2005/4486* (2013.01)

(58) Field of Classification Search
CPC combination set(s) only.
See application file for complete search history.

(56) References Cited

U.S. PATENT DOCUMENTS

| 4,121,589 | A | * | 10/1978 | McDonnell | A61F 5/441 604/328 |
| 4,217,664 | A | * | 8/1980 | Faso | A61F 2/0063 600/32 |
| 4,834,731 | A | * | 5/1989 | Nowak | A61F 5/448 604/339 |
| 4,834,732 | A | * | 5/1989 | Steer | A61F 5/448 604/338 |
| 4,883,477 | A | * | 11/1989 | Steer | A61F 5/448 604/339 |
| 4,889,534 | A | * | 12/1989 | Mohiuddin | A61F 5/448 604/339 |

(Continued)

FOREIGN PATENT DOCUMENTS

EP 0145161 A2 6/1985
EP 0255310 A1 2/1988

(Continued)

*Primary Examiner* — Guy K Townsend
(74) *Attorney, Agent, or Firm* — Lambert Shortell & Connaughton; David J. Connaughton, Jr.; Justin P. Tinger

(57) ABSTRACT

An ostomy device for attachment (coupling) to a base plate is disclosed. The ostomy device comprises attachment structures for attachment to a base plate, wherein the ostomy device comprises an attachment ring configured to be detachably attached to the base plate. The ostomy device comprises additional structures provided with attachment elements configured to be detachably attached to the attachment ring. The attachment ring is configured to be detachably attached to the inner side of an attachment recess provided in the locking flange of the base plate.

15 Claims, 11 Drawing Sheets

(56) References Cited

U.S. PATENT DOCUMENTS

| | | | | |
|---|---|---|---|---|
| 4,892,530 A * | 1/1990 | Steer | A61F 5/448 604/338 |
| 4,923,452 A | 5/1990 | Hunger | |
| 4,929,245 A * | 5/1990 | Holtermann | A61F 5/448 604/338 |
| 4,950,261 A * | 8/1990 | Steer | A61F 5/448 604/339 |
| 5,041,102 A * | 8/1991 | Steer | A61F 5/448 604/338 |
| 5,178,615 A * | 1/1993 | Steer | A61F 5/448 604/338 |
| 5,312,381 A * | 5/1994 | Brooks | A61F 5/448 604/332 |
| 5,496,297 A * | 3/1996 | Olsen | A61F 5/448 604/339 |
| 5,843,053 A * | 12/1998 | Steer | A61F 5/448 604/342 |
| 5,902,295 A * | 5/1999 | Steer | A61F 5/448 604/339 |
| 6,537,261 B1 * | 3/2003 | Steer | A61F 5/448 604/342 |
| 8,092,437 B2 * | 1/2012 | Cline | A61F 5/448 604/337 |
| 8,142,406 B2 * | 3/2012 | Blum | A61F 5/445 604/338 |
| 9,517,157 B2 * | 12/2016 | Hanuka | A61F 5/445 604/333 |
| 2004/0073179 A1 * | 4/2004 | Andersen | A61F 5/445 604/338 |
| 2004/0193122 A1 * | 9/2004 | Cline | A61F 5/448 604/332 |
| 2007/0129695 A1 * | 6/2007 | Blum | A61F 5/448 604/338 |
| 2008/0269698 A1 * | 10/2008 | Alexander | A61F 5/445 604/332 |
| 2010/0241093 A1 * | 9/2010 | Hooper | A61F 5/448 604/339 |
| 2012/0109086 A1 * | 5/2012 | Tsai | A61F 5/448 604/335 |
| 2012/0179124 A1 * | 7/2012 | Nguyen-Demary | A61F 5/445 604/333 |
| 2013/0053803 A1 * | 2/2013 | Willoughby | A61F 5/448 604/337 |
| 2014/0213995 A1 | 7/2014 | Garrettson | |
| 2014/0364823 A1 * | 12/2014 | Nguyen-Demary | A61F 5/448 604/333 |
| 2015/0141944 A1 * | 5/2015 | Hanuka | B31B 50/26 604/337 |
| 2018/0235802 A1 * | 8/2018 | Nguyen-Demary | A61F 5/448 604/333 |
| 2018/0344506 A1 * | 12/2018 | Larsen | A61F 5/448 604/333 |

FOREIGN PATENT DOCUMENTS

| | | |
|---|---|---|
| EP | 0334489 A2 | 9/1989 |
| EP | 0381393 A1 | 8/1990 |
| EP | 0821925 A2 | 2/1998 |
| GB | 2201346 A | 9/1988 |
| GB | 2219507 A | 12/1989 |
| GB | 2265832 A | 10/1993 |
| WO | 9418919 | 9/1994 |
| WO | 2011031822 | 3/2011 |
| WO | 20120583388 A1 | 5/2012 |
| WO | 2014110645 | 7/2014 |

* cited by examiner

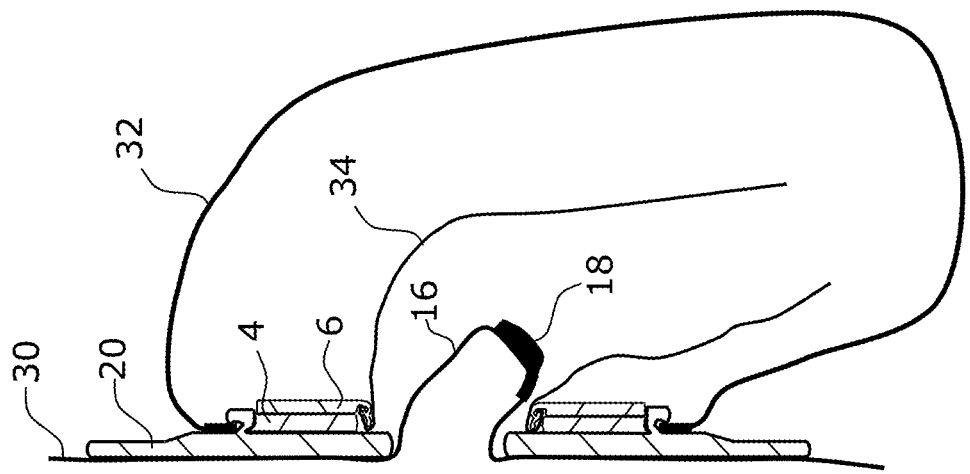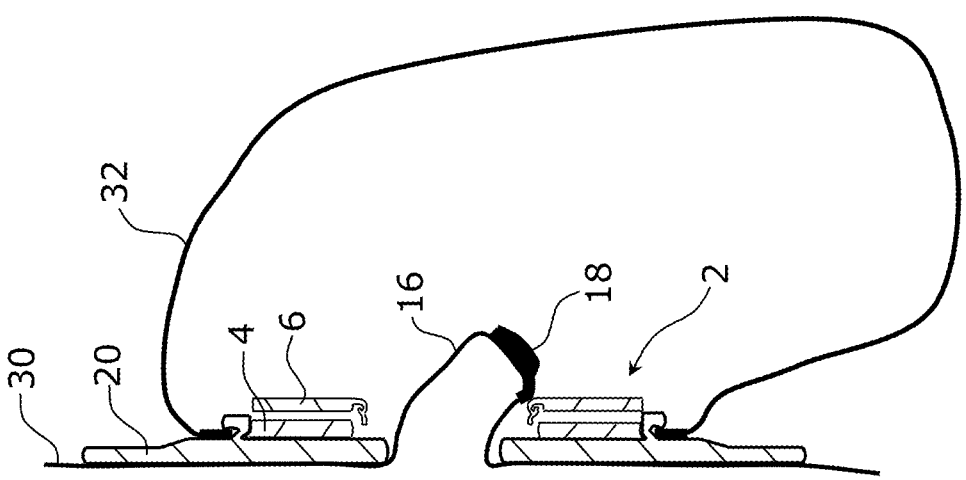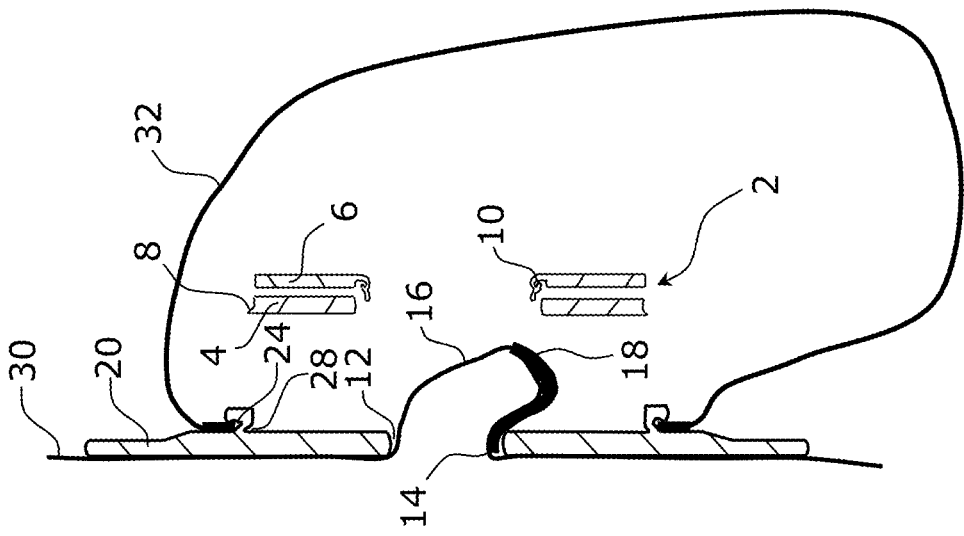

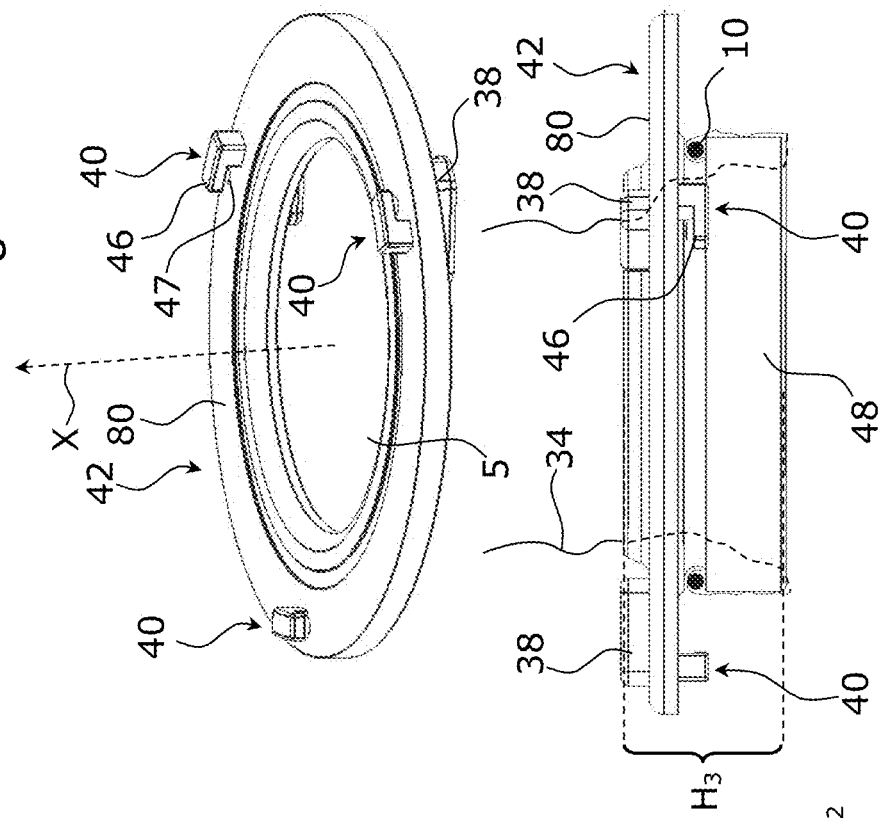
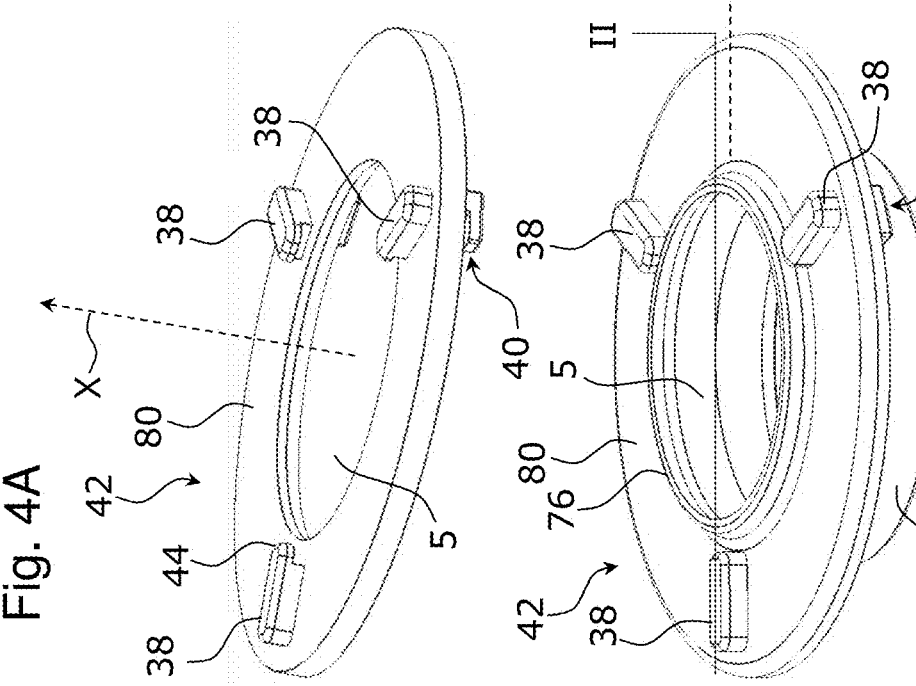

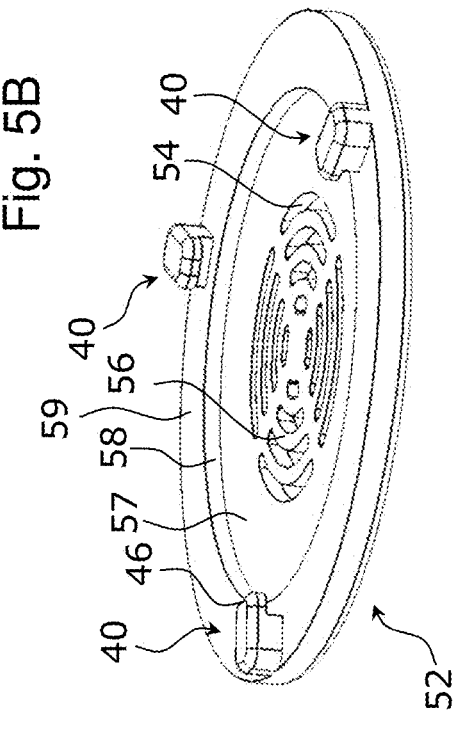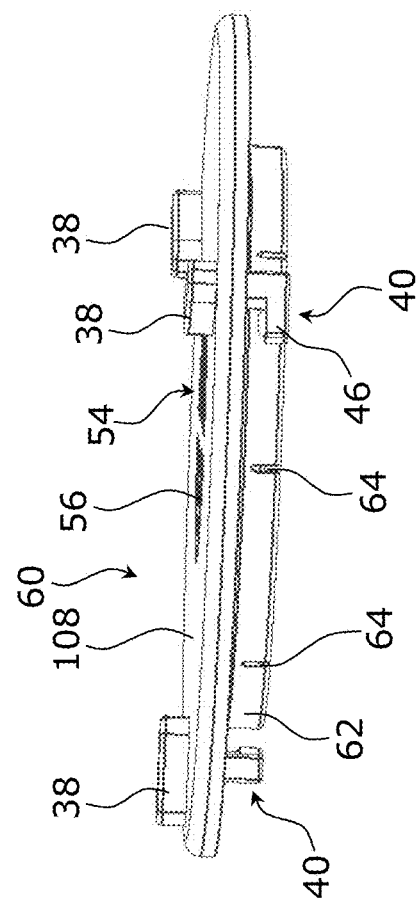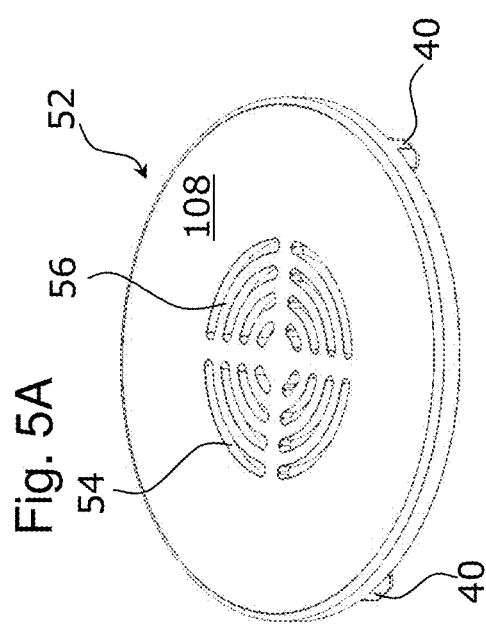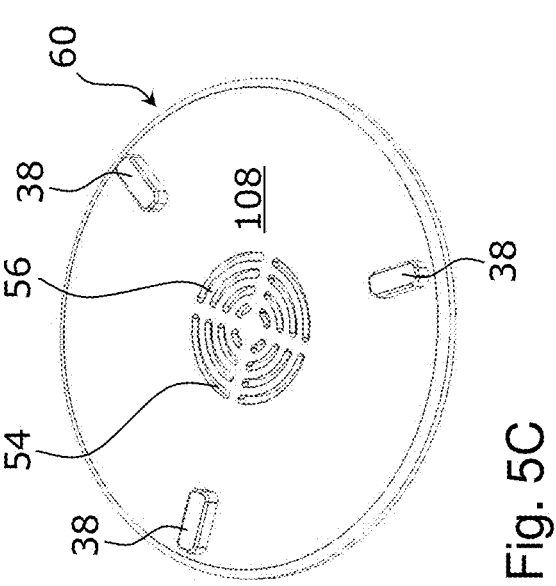

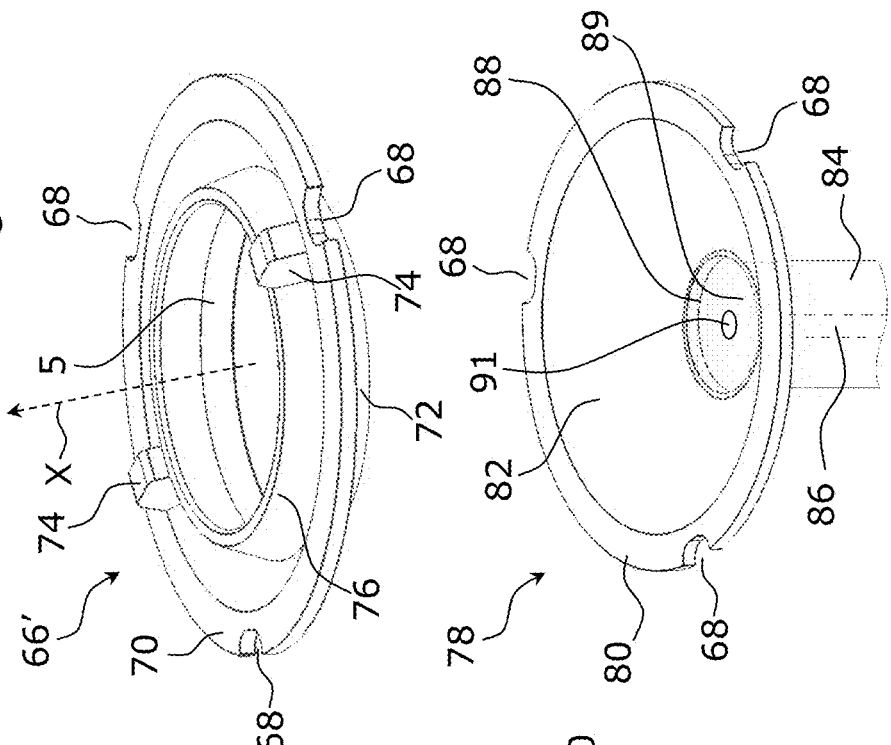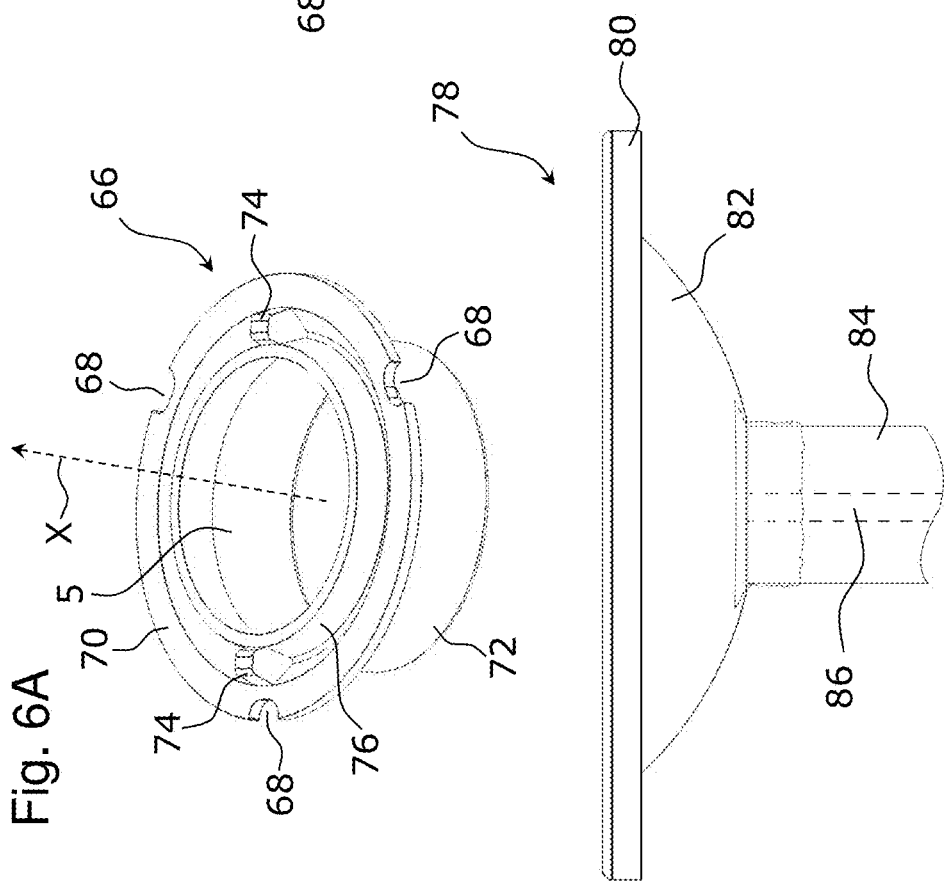

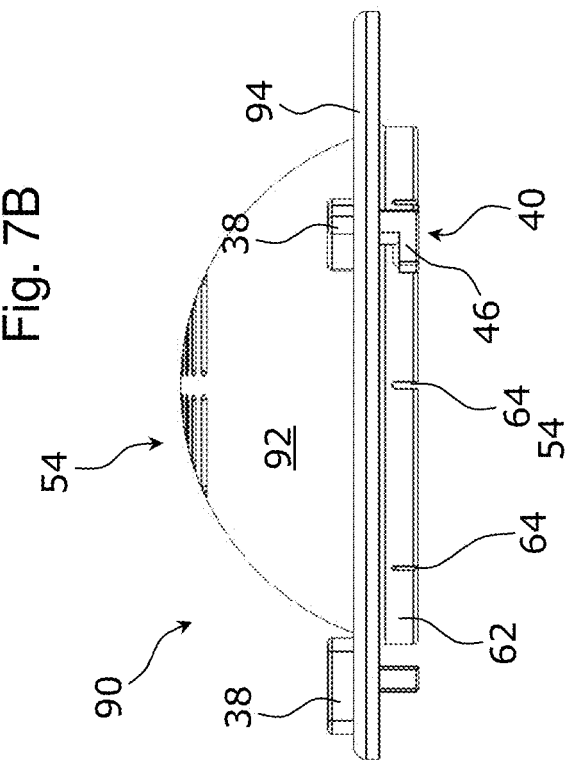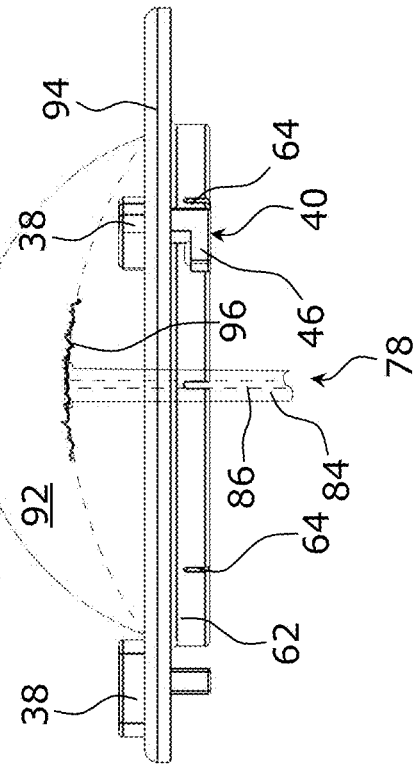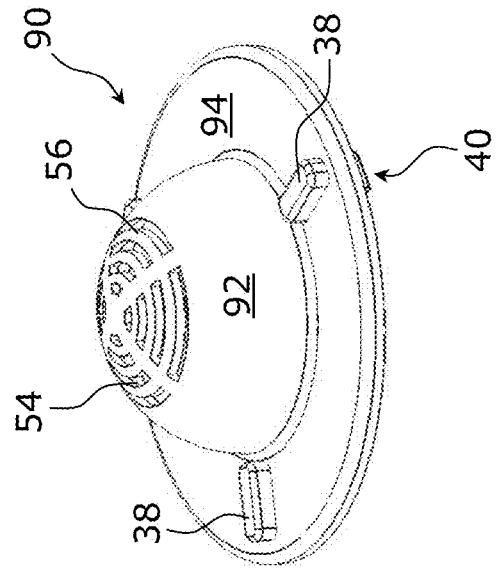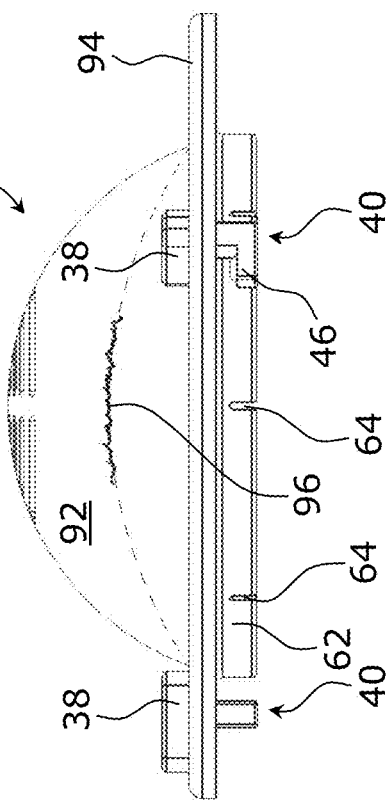

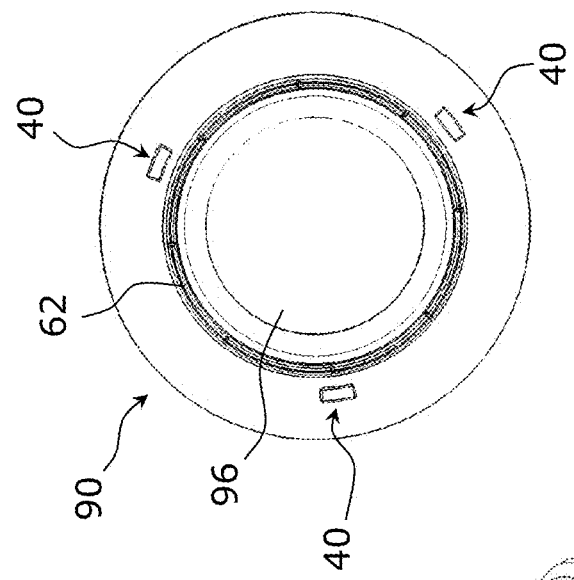
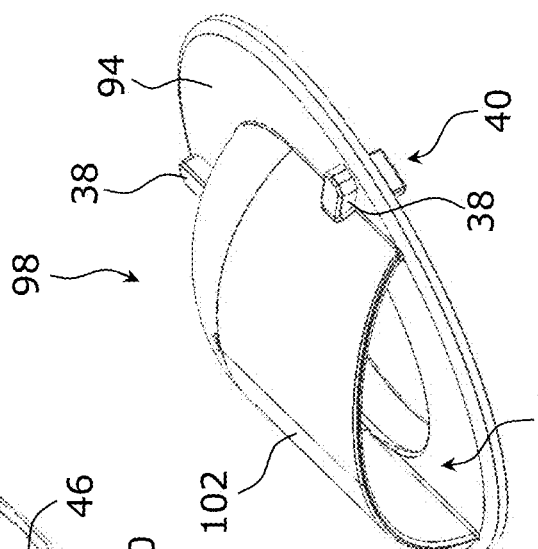
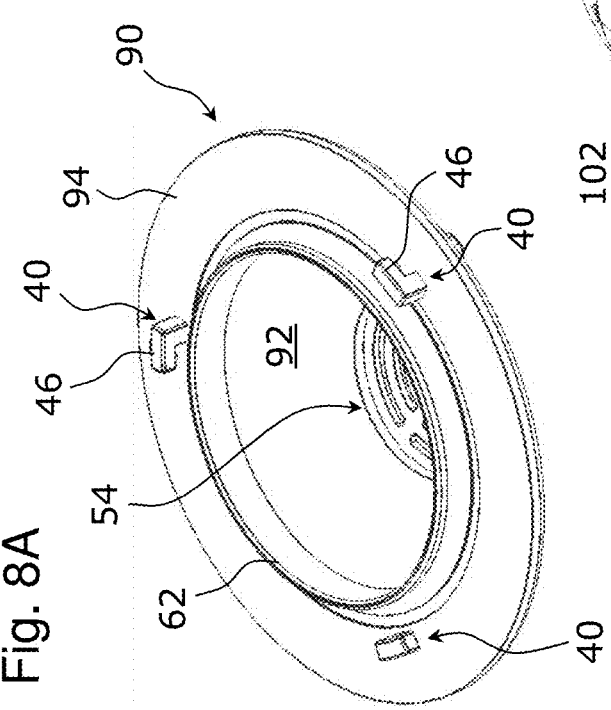

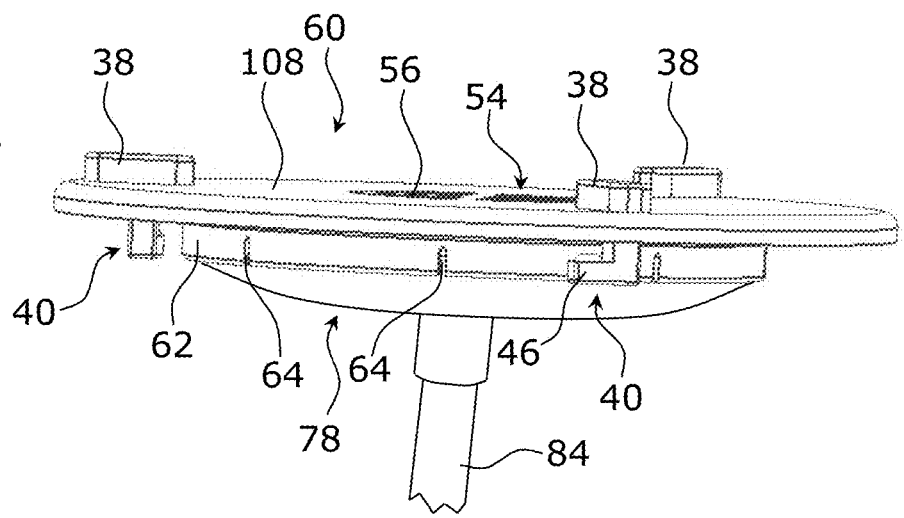
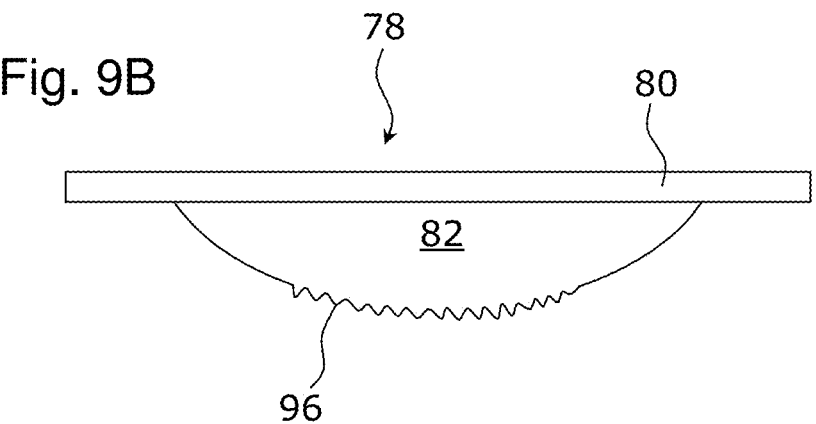
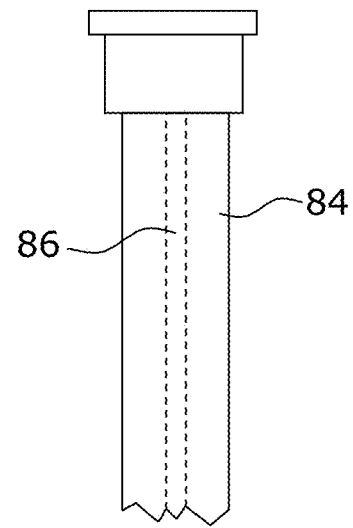

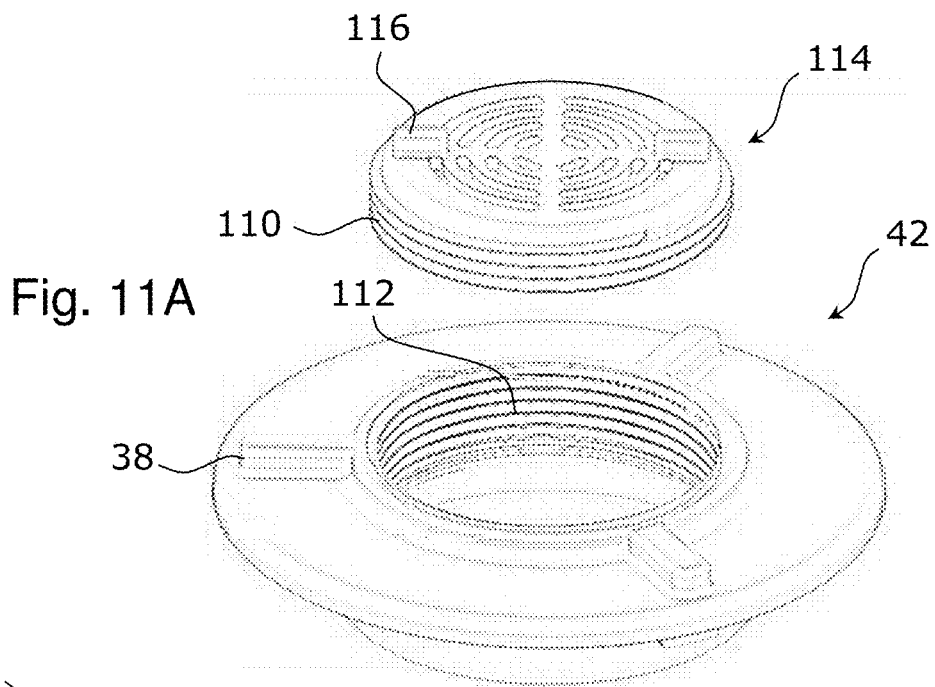
Fig. 11A
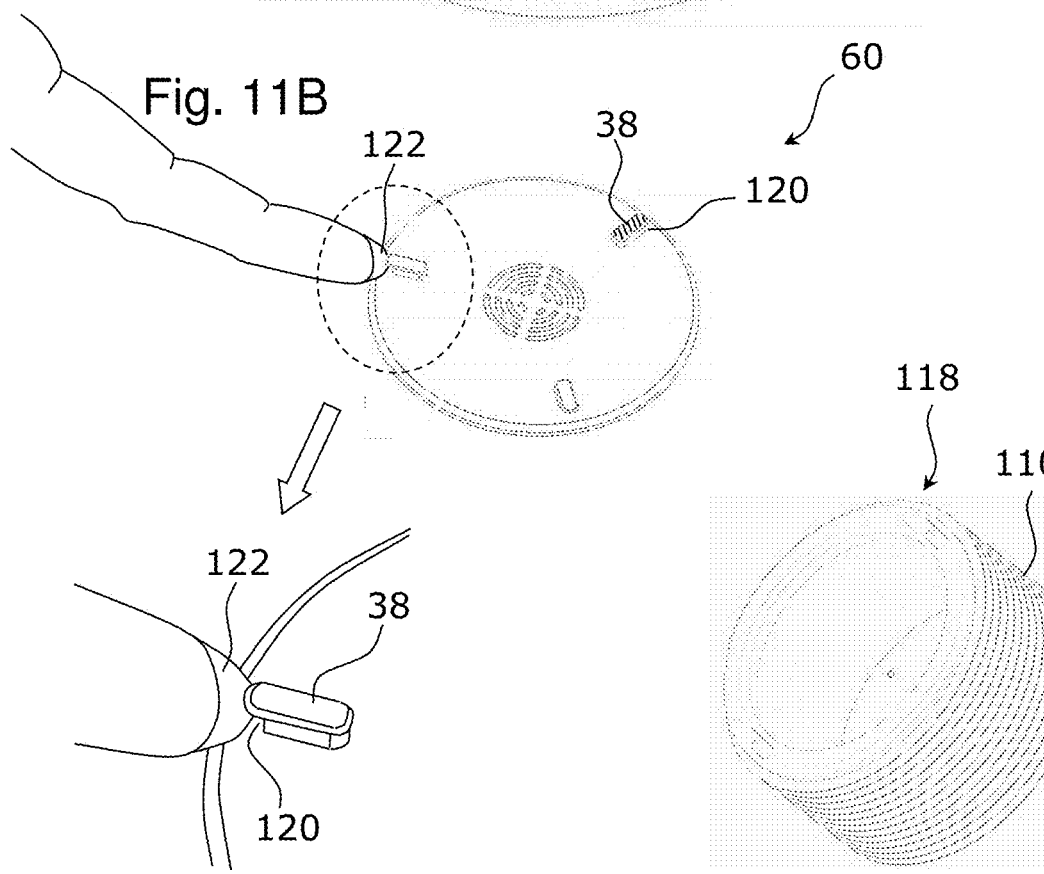
Fig. 11B
Fig. 11C
Fig. 11D

OSTOMY DEVICE

FIELD OF INVENTION

The present invention relates to a device for use in connection with ostomy/stoma. More particularly, the invention relates to a device to be used together with a base plate in order to prevent or alleviate or relieve damage to the skin area caused by urine or stomal discharge.

PRIOR ART

In connection with certain diseases such as carcinomas of the colon or rectum, the surgical removal of the bowel (colostomy) or small intestine (ileostomy) or parts thereof is often necessary. After surgery, an artificial opening is created allowing faeces or urine, either from the intestine or the urinary tract, to pass. Discharge from the ileostomy or colostomy is collected in a stoma pouch.

Ostomy can be performed in different ways. The most common ostomies include colostomy, ileostomy and urostomy, respectively. In a colostomy operation, part of the colon is brought to the surface of the abdomen to form the stoma. There are two types of colostomy, namely end colostomy and loop colostomy. End colostomy is typically performed if parts of the colon and rectum have been removed. Loop colostomy is typically performed as a temporary measure in acute situations, and by this operation, part of the colon is lifted above skin level and held in place with a stoma rod. In an ileostomy operation, a part of the small intestine (the ileum) is brought to the surface of the abdomen to form the stoma. An ileostomy is typically created in cases where the end part of the small intestine is diseased, and may be performed as either an end ileostomy or a loop ileostomy. End ileostomy is made in cases where part of the colon is removed (or need to rest), and the end of the small intestine is brought to the surface of the abdomen to form the stoma. In a loop ileostomy, a loop of the small intestine is lifted above skin level and held in place with a stoma rod. A loop ileostomy may be temporary and performed to protect a surgical join in the bowel. By urostomy, an isolated part of the intestine is brought onto the surface of the abdomen and the other end is sewn up, and the ureters are detached from the bladder and reattached to the isolated section of the intestine. Because this section of the intestine is too small to function as a reservoir, and there is no muscle or valve to control urination, a urostomy pouch to collect the urine is needed.

It is known in the art to apply base plates (so-called skin plates) in connection with stomas. The plates are usually fastened to the skin by an adhesive. The plates have an orifice (or it may be possible to provide an orifice) through which the stoma can be transferred. Several types of pouches to fit the base plate are known in the art.

However, discharge from the stoma may leak to the underneath of the adhesive of the base plate, thus, resulting in skin irritation around the stoma, and may result in the malfunction of the stomal pouch.

Thus, it is desirable to provide a device capable of limiting or eliminating the discharge from leaking and be brought in contact with the skin.

Furthermore, it is desirable to be able to restrain the stoma for a period (e.g. for up to six hours), however, still allowing the gas produced by the stoma to be released.

EP 0 381 393 A1 relates to a coupling element for an ostomy bag. The element comprises a channel-shaped member, a body-side coupling element, and a locking member. The body-side coupling element has a stomal orifice surrounded by a rib-like member for snap-fit engagement with the channel member, and a locking member having a radially inwardly deformable arm and being rotatable relative to the body-side coupling. The coupling element is fixed in the axial direction by rotation of the locking member.

GB 2 201 346 A relates to an ostomy device comprising a body side coupling ring connected to a bag side coupling ring by an intermediate locking ring which can be rotated relative to one of the body side and bag side coupling rings, thereby permitting the bag side ring to be separated from the body side ring.

GB 2 219 507 A relates to an ostomy bag coupling comprising a body side coupling having first seal means, and a body side support means (base plate) supporting the first seal means, and a bag side coupling having second seal means, whereby on engagement of the first and second seal means and relative rotation of the support means, the coupling is releasably locked against separating movement.

However, the ostomy devices known from EP 0 381 393 A1, GBB 2 201 346 A and GB 2 219 507 A, respectively, cannot be used with conventionally used and commercially available base plates. Accordingly, it is desirable to provide an ostomy device which may be used with such commercially available base plates.

OBJECTS OF THE INVENTION

It in an object of the present invention to provide an ostomy device capable of reducing or even eliminating the risk of the skin being exposed to urine and faeces.

It is a further object of the invention to provide an ostomy device, which device may by locked for a prolonged period of time maintaining gas release from the stomal aperture.

It is an even further object of the present invention to provide an ostomy device which may be used with commercially available base plates.

SUMMARY OF THE INVENTION

The objects of the present invention can be achieved by an ostomy device as defined in the independent claims. Preferred embodiments are defined in the dependent sub claims, explained in the following description and illustrated in the accompanying drawings. By the present invention, an ostomy device is provided, which device reduces or eliminates contact by the ostomy discharge such as urine and faeces with the skin.

The ostomy device according to the invention is an ostomy device for attachment (coupling) to a base plate, wherein the ostomy device comprises attachment structures for attachment to a base plate, wherein the ostomy device comprises an attachment ring configured to be detachably attached to the base plate, wherein the ostomy device comprises additional structures provided with attachment elements configured to be detachably attached to the attachment ring, wherein the attachment ring is configured to be detachably attached to the inner side of an attachment recess provided in the locking flange of the base plate.

Hereby, the invention makes it possible to provide an ostomy device capable of restraining (sealed off/close) the stoma for a period (e.g. for up to six hours), in a manner in which the gas produced by the stoma can be released.

The ostomy device comprises attachment structures for attachment to a base plate, wherein the ostomy device comprises an attachment ring configured to be detachably attached to the base plate, wherein the ostomy device comprises additional structures provided with attachment elements configured to be detachably attached to the attachment ring, wherein the attachment ring is configured to be detachably attached to the inner side of an attachment recess provided in the locking flange of the base plate. Hereby, the ostomy device according to the invention is configured to use a commercially available Istandard base plate as a mounting base.

The ostomy device comprises attachment structures for attachment to a base plate. These attachment structures may be part of an attachment ring configured to be detachably attached to the base plate.

The ostomy device comprises additional structures provided with attachment elements configured to be detachably attached to the attachment ring. Hereby, it is possible to attach one or more additional structures to the attachment ring attached to the base plate.

It may be an advantage that the ostomy device comprises an attachment ring configured to be detachably attached to the base plate by means of an attachment profile (structure) configured to be mounted in an attachment recess in the base plate.

Hereby, a fast, simple and secure attachment of an attachment ring can be achieved.

It may be an advantage that an attachment profile shaped as a thin, ring-shaped disc arranged on the periphery of the attachment ring, is provided on the attachment ring. It is preferred that the attachment profile is configured to engage with a corresponding attachment recess provided in the base plate.

The attachment profile may preferably be shaped as portions of a ring, e.g. two ring portions each constituting a quarter of a ring (extending along 90°) of the disc arranged on the periphery of the attachment ring, or four ring portions each constituting an eighth part (extending along 45°) of a ring of the disc arranged on the periphery of the attachment ring.

It may be advantageous that the ostomy device comprises a closing disc, wherein the closing disc comprises a structure configured to mount a tube, wherein the closing disc is configured to be detachably attached to the attachment ring.

Hereby, it is possible to mount a tube to the closing disc and guide urine or stomal discharge through the tube.

It may be an advantage that the closing disc comprises a cylindrical portion arranged centrally and extending axially and coaxial with respect to a ring-shaped outer part surrounding the centrally arranged cylindrical portion.

It may be beneficial that the ostomy device comprises a ventilated cap configured to be detachably attached to the attachment ring.

Hereby, it is possible to release gas from the stoma.

It may be an advantage that the ventilated cap comprises structures configured to be detachably attached to the attachment ring. These structures may comprise attachment elements configured to engage corresponding mounting holes provided in the attachment ring.

It may be advantageous that the ventilated cap comprises a central portion comprising a section of a sphere and a ring-shaped portion arranged outside (surrounding) the central portion, wherein the ring-shaped portion comprises a number of attachment elements configured to engage the attachment ring. The ring-shaped portion may comprise a number of attachment elements configured to engage mounting holes provided in the attachment ring.

It may be an advantage that the ventilated cap comprises a filter integrated in the ventilated cap.

Hereby, it is possible to reduce or even eliminate the foul smell from gas released through the stoma. Furthermore, it is possible to muffle the sound generated when evacuating gas through the stoma.

It may be an advantage that the cap is configured to be mounted on a (e.g. circular plate-shaped) ventilated disc. Accordingly, the ventilated disc may constitute an additional filter device hereby increasing the total filtering capacity.

It may be advantageous that the ostomy device comprises one or more rotatable knobs provided on the top side of one of the additional structures, wherein each rotatable knob is configured to lockingly engage a corresponding structure.

Accordingly, it is possible to lock the ostomy device and hereby secure that the coupled parts remain attached to each other. On the other hand, it is also possible to disengage the parts from each other in a fast, simple and user-friendly manner.

It may be beneficial that the ostomy device comprises an additional structure provided with one or more recesses configured to engagingly receive one or more attachment element and/or protrusions, wherein the additional structure is configured to be axially locked by rotating the additional structure in such a manner that the one or more attachment element and/or protrusions are displaced with respect to the recesses.

It may be an advantage that the ostomy device comprises a plug member comprising a ring portion constituting the upper periphery of the plug member, wherein a bowl-shaped portion extends under the ring portion, wherein a basically centrally arranged opening is provided in the bowl-shaped portion, wherein the ostomy device comprises a pipe having a through-going air canal, wherein the pipe is configured to be inserted into a stoma, wherein the pipe is configured to evacuate gas from the stoma through the opening.

Hereby, it is possible to provide a safe and efficient plugging of the stoma and at the same time make it possible to plug the stoma in a prolonged period of time in a manner in which it is possible to release gas from the stoma.

It may be an advantage that the ostomy device comprises a closing ring comprising a basically cylindrical contact wall, wherein a flange is provided in the proximal end of the cylindrical contact wall, wherein a tapered ring structure is provided in the proximal end of the contact wall, wherein a centrally arranged opening is provided in the closing ring.

It may be beneficial that two opposing protrusions are provided between the tapered ring structure and the flange, wherein the protrusions are configured to be accessed in order to rotate the closing ring about its longitudinal axis when the closing ring is attached to an object (e.g. via mechanical engagement with corresponding protrusions on attachment elements of the element).

It may be advantageous that the ostomy device comprises an open cap, wherein the open cap comprises a pipe portion provided with an opening.

It may be an advantage that the pipe portion is attached to a flat, circular ring-shaped portion.

It may be beneficial that three knobs are rotatably attached to the ring-shaped portion. The knobs are preferably evenly distributed along the periphery of the ring-shaped portion.

DESCRIPTION OF THE DRAWINGS

The invention will become more fully understood from the detailed description given herein below. The accompanying drawings are given by way of illustration only, and thus, they are not limitative of the present invention. In the accompanying drawings:

FIG. 2A shows a schematic cross-sectional view of an ostomy device according to the invention;

FIG. 2B shows a schematic cross-sectional view of the ostomy device shown in FIG. 2A;

FIG. 2C shows a schematic cross-sectional view of the ostomy device shown in FIG. 2A and FIG. 2B, however, in another configuration;

FIG. 4A shows a perspective top view of a closing disc according to the invention;

FIG. 4B shows a perspective bottom view of the closing disc shown in FIG. 4A;

FIG. 4C shows a perspective top view of a closing disc according to the invention;

FIG. 4D shows a cross-sectional perspective view of the closing disc shown in FIG. 4C;

FIG. 5A shows a perspective top view of a ventilated cap according to the invention;

FIG. 5B shows a perspective bottom view of the ventilated cap shown in FIG. 5A;

FIG. 5C shows a ventilated cap according to the invention;

FIG. 5D shows a side view of the ventilated cap shown in FIG. 5C;

FIG. 6A shows a perspective top view of a closing ring according to the invention;

FIG. 6B shows a perspective top view of another closing ring according to the invention;

FIG. 6C shows a side view of a plug member according to the invention;

FIG. 6D shows a perspective view of the plug member shown in FIG. 6C;

FIG. 7A shows a perspective view of a ventilated cap according to the invention;

FIG. 7B shows a side view of the ventilated cap according to the invention;

FIG. 7C shows a schematic view of the ventilated cap shown in FIG. 7B;

FIG. 7D shows a schematic view of a ventilated cap;

FIG. 8A shows a perspective view of a ventilated cap that basically corresponds to the one shown in FIG. 7A and FIG. 7B;

FIG. 8B shows a ventilated cap corresponding to the one shown in FIG. 8A;

FIG. 8C shows an open ventilated cap according to the invention;

FIG. 9A shows an open ventilated cap provided with a plug member;

FIG. 9B shows a plug cap according to the invention;

FIG. 9C shows a schematic view of a pipe for the plug cap shown in FIG. 9B;

FIG. 11A shows a closing disc according to the invention;

FIG. 11B shows a ventilated cap according to the invention;

FIG. 11C shows a close-up view of the ventilated cap shown in FIG. 11B and

FIG. 11D shows a cylindrical member according to the invention.

DETAILED DESCRIPTION OF THE INVENTION

Referring now in detail to the drawings for the purpose of illustrating preferred embodiments of the present invention, an ostomy device 2 according to the invention is illustrated in FIG. 2.

Figure 1:
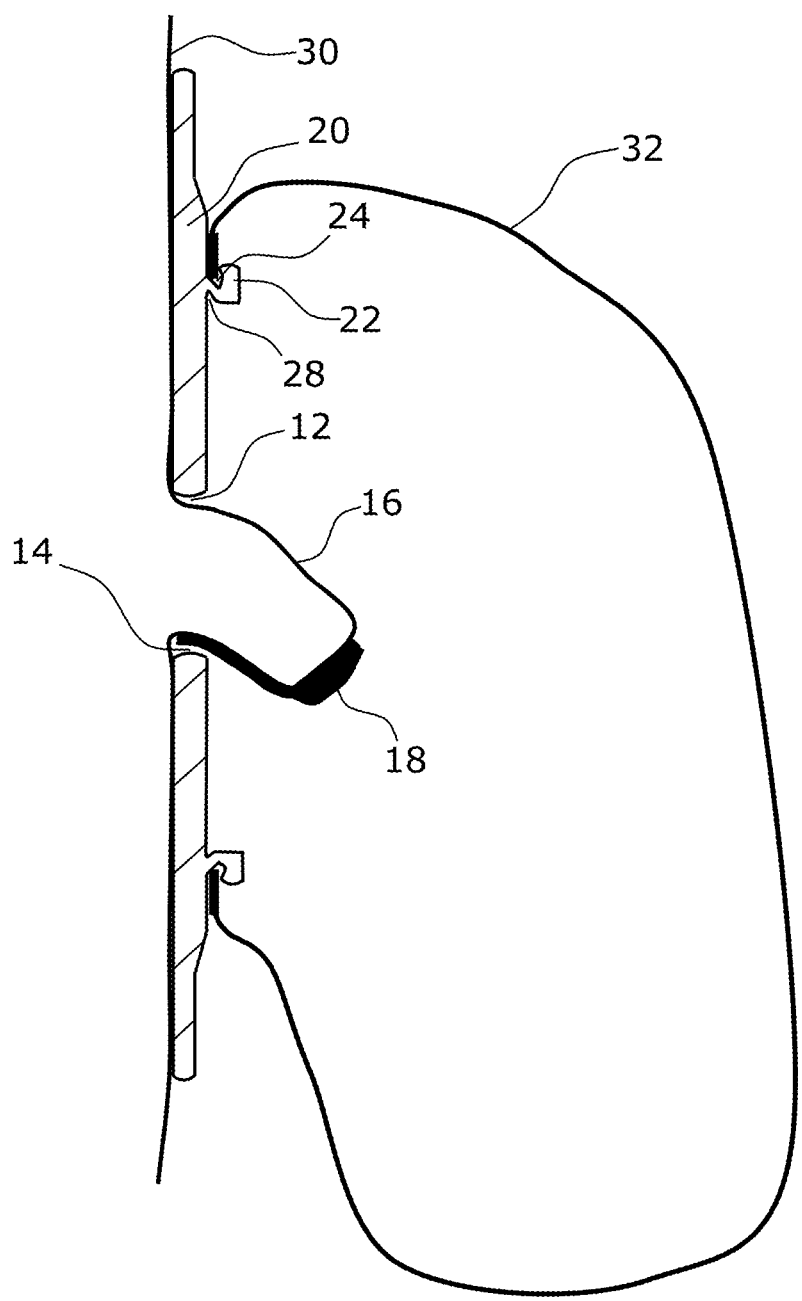
FIG. 1 shows a schematic view of a convention system suitable for stoma patients.

FIG. 1, however, illustrates a conventional system suitable for stoma patients. FIG. 1 illustrates a cross-sectional view of a system comprising a base plate 20 attached to the skin 30 of the user of the system. The base system comprises an oval and flat sticky portion configured to be attached to the skin 30.

The base plate 20 furthermore comprises a locking flange 22 configured to engagingly receive an ostomy bag 32 for receiving bodily waste materials such as faeces 18 and urine. The ostomy bag 32 is configured to be attached by means of a click coupling provided between the coupling ring 26 of the ostomy bag 32 and the locking recess 24 of the flange 22.

Since a gap is provided between the stoma 16 and the base plate 20, there is a risk for urine and faeces 18 from the stoma 16 can be brought into contact with the skin 30 in the exposed area 14 between the stoma 16 and the base plate 20. Urine and faeces 18 present in the exposed area 14 will potentially give rise to irritated skin and in certain situations eczema (rash) or wounds. Such symptoms are undesirable and therefore is a need for an alternative to the conventional (prior art) solution (as the one indicated in FIG. 1).

FIG. 2 illustrates a cross-sectional view of an ostomy device 2 according to the invention. The ostomy device 2 is attached to a conventional base plate 20 by means of a locking recess 24 provided in the base plate 20.

An attachment ring 4 and a connection element 6 shaped as a connection ring 6 are provided at the right side of the base plate 20. Attachment structures (not shown) are provided in the attachment ring 4 and in the connection element 6, respectively. Accordingly, the attachment ring 4 and the connection element 6 can be mechanically attached to each other.

An attachment profile 8 shaped as a thin ring-shaped disc attached to the periphery of the attachment ring 4 is provided at the attachment ring 4. The attachment profile 8 is configured to lockingly engage with a corresponding attachment recess 28 provided in the base plate 20.

An attachment bending 10 configured to attach a tube (e.g. a latex tube as shown in FIG. 2C) is provided on the connection ring 6.

The ostomy device 2 comprises two separate portions: the attachment ring 4 and the connection element 6, which is configured to be mechanically attached to each other. It is, however, possible to provide an ostomy device 2, wherein the two portions 4, 6 are formed as a one-piece body. In this embodiment, the one-piece body will be configured to be attached to the base plate 20.

It is possible to provide the base plate 20 with alternatively shaped attachment structures. Such alternatively shaped attachment structures may comprise all suitable mechanical structures including attachment pins, recesses, tracks (e.g. corresponding tongue and groove structures).

In FIG. 2A, it can be seen that there is access for urine and faeces 18 in the exposed area 14 between the stoma 16 and the base plate 20, due to the gap provided there between.

FIG. 2B illustrates a cross-sectional view of the ostomy device 2 shown in FIG. 2A. The ostomy device 2 is shown in a configuration, in which the attachment ring 4 is mounted and hereby attached to the base plate 20. The attachment profile 8 (see FIG. 2A) of the attachment ring engages the attachment recess 28 of the base plate 20. On the contrary, the connection element 6 has not yet been attached to the attachment ring 4. The connection ring 6 is arranged at the right side of the attachment ring 4 attached to the base plate 20.

FIG. 2C illustrates a cross-sectional view of the ostomy device 2 as shown in FIG. 2A and FIG. 2C in a configuration, in which the attachment ring 4 is mounted and hereby attached to the base plate 20 and wherein the connection element 6 is attached to the attachment ring 4. The fixation of the connection element 6 to the attachment ring 4 can be provided by using different types of attachment structures (not shown), e.g. by means of a number of attachment recesses provided in the attachment ring 4, wherein the attachment recesses are configured to engage with corresponding engaging structures provided in the connection element 6.

A tube (that preferably may be a tube made in latex) is attached to the connection element 6. One end of the tube 34 is attached to an attachment bending 10 provided in the connection ring 6. The tube 34 prevents the stomi 16 from direct contact with the connection element 6.

On FIG. 2B and FIG. 2C it can be seen that the stomi 16 is slightly raised compared to the configuration shown in FIG. 2A due to the mounting of the attachment ring 4 and the connection element 6. Hereby, it is possible to reduce or even completely eliminate the risk of the exposed area (14 shown in FIG. 2A) provided between the stoma 16 and the base plate 20 being exposed to urine and faeces 18. This effect can be increased by extending the axial extension (thickness) of the attachment ring 4 and the connection element 6, respectively, or by mounting additional elements on the attachment ring 4 and/or the connection element 6.

Figures 3A, 3B, 3C, 3D:
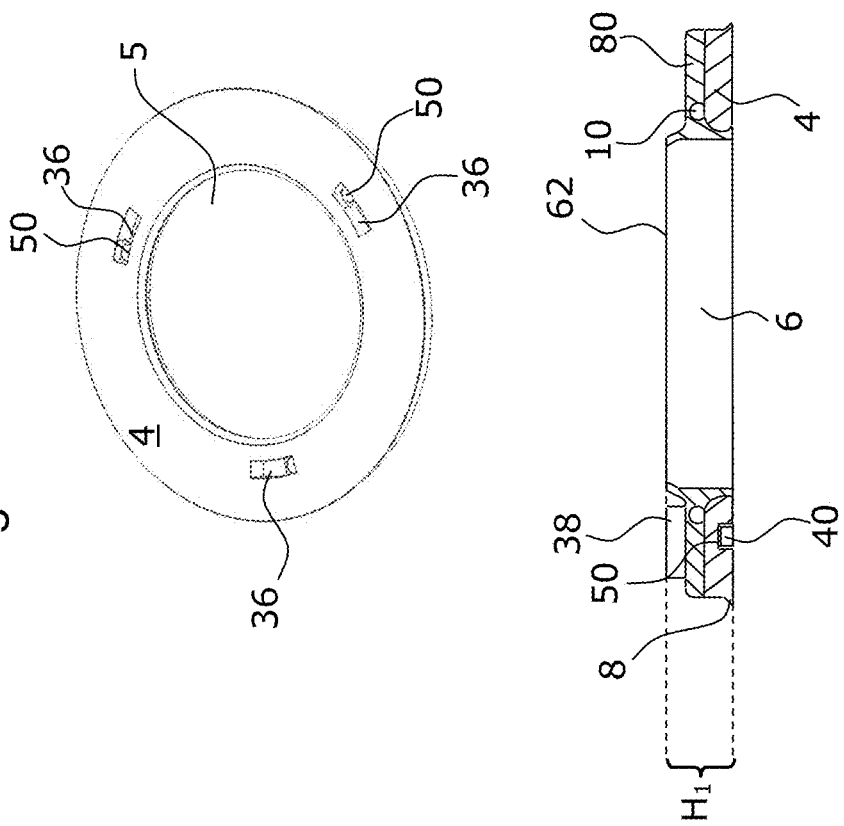
FIG. 3A shows a perspective top view of an attachment ring according to the invention.
FIG. 3B shows a perspective bottom view of the attachment ring shown in FIG. 3A.
FIG. 3C shows a perspective bottom view of a connection element attached to an attachment ring according to the invention.
FIG. 3D shows a cross-sectional perspective view of the connection element shown in FIG. 3C.

FIG. 3A illustrates a perspective top view of an attachment ring 4 according to the invention. A centrally arranged circular opening 5 for receiving the stoma (see FIG. 2B and FIG. 2C) is provided in the attachment ring 4. Three mounting holes 36 are evenly distributed along the attachment ring 4. These mounting holes 36 are configured to receive corresponding attachment elements (40 see FIG. 3B). The mounting holes 36 extend tangentially close to the inner periphery of the attachment ring 4.

FIG. 3B illustrates a perspective bottom view of the attachment ring 4 shown in FIG. 3A. It can be seen that a centrally arranged circular opening 5 and three mounting holes 36 are provided in the attachment ring 5. A concave contact surface 50 configured to bear against a corresponding attachment element (40 see FIG. 3B) is provided in each mounting hole 36. The corresponding attachment element is configured to lockingly engage with the concave contact surface 50 and hereby prevent axial displacement with respect to the attachment ring 4.

FIG. 3C illustrates a perspective view of a connection element 6 attached to an attachment ring 4 according to the invention. A centrally arranged circular opening 5 is provided in the attachment ring 5. Three (rotatably attached) knobs 38 are evenly distributed along the ring portion 80 of the connection element. The knobs 38 extend radially and are essentially box-shaped. The knobs 38 are attached to the attachment element 40 provided at the bottom side of the connection element 6 (see FIG. 3D). A tubular portion 62 is provided along the inner periphery of the attachment ele-ment. The attachment ring 4 is configured to function as a closing disc adapted to seal against the stoma. The attachment ring 4 is configured to receive a tube (e.g. a latex tube) as illustrated in FIG. 2C. The tube may be mounted in attachment structures (e.g. attachment bendings) 10 (see FIG. 3D). It can be seen that an attachment profile 8 shaped as a thin, ring-shaped disc provided at the periphery of the attachment ring 4, is provided at the attachment ring 4, wherein the disc is configured to engage with a corresponding attachment recess 28 provided in a base plate (see FIG. 2A, FIG. 2B and FIG. 2C).

FIG. 3D illustrates a cross-sectional view of the connection element 6 shown in FIG. 3C, wherein the connection element 6 is attached to an attachment ring 4. It can be seen that the attachment element 40 of the connection element engages the concave contact surface 50 of the mounting hole of the attachment ring.

It can be seen that the attachment structures 10 have a circular sectional cross-section configured to receive the edge/periphery of a latex tube (as shown in FIG. 2C). When the two portions: the connection element 6 and the attachment ring 4 are attached to each other, the latex tube will be locked.

The tube can, due to its flexibility, be mounted on the connection element 6 and thus be attached to the connection element 6.

It can be seen in FIG. 3D that the rotatable knobs 38 provided on the connection element 6 as well as the upper portion of the tubular portion 62 protrude from the ring portion 80 of the connection element 6. The height $H_1$ of the connection element 6 is indicated on FIG. 3D.

FIG. 4A illustrates a perspective top view of a closing disc 42 according to the invention. The locking disc 42 comprises a thin ring-shaped disc provided with a centrally arranged circular opening 5. Three radially extending knobs 38 are provided on the top surface of the ring-shaped disc. The knobs 38 are evenly distributed along the top surface of the disc. Each of the three knobs 38 are connected to a corresponding attachment element 40 configured to lockingly engage a corresponding element provided on the construction structure below the closing disc 42.

Accordingly, the knobs 38 are configured be arranged in: a) an open configuration, in which it is possible to axially displace the closing disc 42 and b) a closed configuration, in which the closing disc 42 is prevented from being axially displaced due to the locking (engagement) between the attachment elements 40 and the construction structures arranged below the closing disc 42.

Each knob 38 comprises a protrusion 44. It is possible to apply a base plate provided with attachment elements configured to (lockingly) engage with corresponding attachment elements, e.g. a closing ring 66, 66' as shown in FIG. 6A or FIG. 6B or the plug member shown in FIG. 6D, wherein the protrusions 44 initially are aligned with the recesses 68 (FIG. 6D). Hereafter, the closing ring 66, 66' or the plug member 78 can be closed (locked) relative to the closing disc 42 and its protrusion 44. The longitudinal axis X of the closing disc is illustrated in FIG. 4A.

FIG. 4B illustrates a perspective bottom view of the closing disc 42 shown in FIG. 4A. It can be seen that each of the rotatably attached attachment elements have an L-shaped form comprising a protrusion 46 configured to be brought into mechanical engagement with corresponding structures. The protrusions 46 comprise a convex portion 47 directed towards the ring portion 80 of the closing disc 42. The longitudinal axis X of the closing disc 42 is shown in FIG. 4B.

A central opening 5 is provided in the closing disc 42. Alternatively, it is possible to provide a closing disc without an opening 5. A closed closing disc 42 may comprise a filter configured to muffle the sound generated (when evacuating gas through the stoma) and neutralise foul smell (from gas released through the stoma).

FIG. 4C illustrates a perspective top view of a closing disc 42 according to the invention. The locking disc 42 comprises a thin ring-shaped disc provided with a centrally arranged circular opening 5.

Three radially extending knobs 38 are provided on the top surface of the ring-shaped disc. The knobs 38 are mechanically attached to a rotatably mounted attachment element 40.

The closing disc 42 comprises a tubular portion 48 extending in extension of the opening 5. The closing disc 42 further comprises a tapered ring structure 76 extending in extension of the proximal portion of the tubular portion 48. The height $H_2$ of the closing disc 42 (without the knobs 38, which means from the tubular portion 48 to the top surface of the ring-shaped disc 80) is indicated in FIG. 4C. When comparing with FIG. 3D and FIG. 4C, it can be seen that the height $H_2$ of the closing disc 42, shown in FIG. 4D, is (significantly) larger than the height $H_1$ of the connection element 6 shown in FIG. 3D. The section line (cutting plane line) II is indicated in FIG. 4C.

FIG. 4D illustrates a cross-sectional view (corresponding to the cutting plane II indicated in FIG. 4C) of the closing disc 42 shown in FIG. 4C. A latex tube 34 is attached to the attachment bending 10.

FIG. 5A illustrates a perspective top view of a ventilated disc 52 according to the invention. The ventilated disc 52 comprises a disc 108 provided with a centrally arranged grate structure 56. A filter 54 provided to retain undesired components of the gas released from the stoma, is provided in the opening of the grate structure 56. Alternatively, it is possible to provide the filter 54 below the grate structure 56. The filter 54 reduces or even eliminates the obnoxious smell related to the body produced gas released through the stoma.

Three attachment elements 40 (only two are visible) are provided on the back side of the ventilated disc 54.

The attachment elements 40 are shown in more details in FIG. 4B showing a perspective bottom view of the ventilated disc 52 shown in FIG. 5A.

It can be seen that each attachment element 40 is provided with a protrusion in its distal end. The protrusion is directed inwardly towards the central portion of the ventilated disc 52 in FIG. 5B.

A filter 54 is provided under the opening of the grate structure 56 below the disc-shaped portion 57.

The ventilated disc 52 comprises a ring-shaped portion 59, which is thicker than the disc-formed portion 57 arranged inside the ring-shaped portion 59. Moreover, an inner wall 58 is provided at the position in which the ring-shaped portion 59 borders on the disc-shaped portion 57.

FIG. 5C illustrates a ventilated cap 60 according to the invention. The ventilated cap 60 comprises a disc 108 provided with three rotatably mounted knobs 38. It is possible to mount another number of knobs 38, e.g. two knobs or four knobs 38. It is possible to provide a filtering material in the ventilated cap 60.

The three (rotatably mounted) knobs 38 extend radially towards the centre of the circular disc 108. The knobs 38 are evenly distributed along the periphery of the disc 108. Accordingly, the knobs 38 are arranged about 120 degrees from each other along the periphery of the disc 108.

A grate structure 56, surrounding an underlying filter 54, arranged and positioned in order to filter gas from the stoma and hereby reduce inconvenient smell and sound, is provided centrally at the circular disc 108.

FIG. 5D illustrates a side view of the ventilated cap 60 shown in FIG. 5C. Rotatable knobs 38 each mechanically connected to a corresponding attachment element 40 by a mechanical connection structure (e.g. a common shaft) are attached to the top surface of the disc 108. Each of the attachment elements 40 are rotatably mounted to the disc 108 and are provided at the bottom side of the disc. Each attachment element 40 comprises a distally extending protrusion 46.

In the central area of the circular disc 108 the grate structure 56 and the underlying filter 54 can be seen. A tubular portion 62 provided with a number of recesses 64 extend perpendicular to the bottom side of the disc. The recesses 64 increase the flexibility of the tubular portion and eases the mounting of the tubular portion 62 on a corresponding structure.

Since the tubular portion 62 is cylindrical, the tubular portion 62 is configured to be attached outside a cylindrical structure having a slightly smaller diameter or inside a cylindrical structure having a slightly larger diameter.

FIG. 6A illustrates a perspective top view of a closing ring 66 according to the invention. The closing ring 66 comprises a cylindrical contact wall 72 provided with a flange 70 in its proximal end. Three recesses 68 having a length that is shorter than the periphery of the flange 70 are evenly distributed along the periphery of the flange 70.

A tapered (conical) ring structure 76 is provided in extension of the proximal end of the cylindrical contact wall 72. Two opposing protrusions 74 are provided between the ring element 76 and the flange 70. The protrusions 74 are configured to be used to (operated) in order to rotate the closing ring 66 about its longitudinal axis X when attaching the closing ring 66 to a structure (e.g. by means of mechanical engagement of corresponding protrusions on attachment elements of the structure). The closing ring 66 comprises a centrally arranged opening 5.

FIG. 6B illustrates a perspective top view of another closing ring 66 according to the invention. The closing ring 66 comprises a cylindrical contact wall 72, which is slightly shorter than the one shown in FIG. 6A. Three recesses 68 having a length that is shorter than the periphery of the flange 70 are evenly distributed along the periphery of the flange 70. The closing ring 66 comprises a centrally arranged opening 5.

FIG. 6C illustrates a side view of a plug member 78 according to the invention. The plug member 78 comprises a ring portion 80 constituting the upper periphery of the plug member 78. A bowl-shaped portion 82 provided with a centrally arranged opening 88 (see FIG. 6D) extends below the circular ring portion 80. A pipe 84 having a through-going air canal 86 is attached through the opening 88. The pipe 84 may preferably be produced in a foam material and be configured to be inserted into a stoma in order to plug a colostomy. Air can be evacuated through the through-going air canal 86. It is possible and may be an advantage to arrange a filter (e.g. as illustrated in FIG. 5A) in axial extension of the ring portion 80.

FIG. 6D illustrates a perspective view of the plug member 78 shown in FIG. 6C. It can be seen that the plug member 78 comprises a bowl-shaped (concave) portion 82 provided with a centrally arranged opening 88. Three recesses 68 are evenly distributed along the periphery of the ring portion 80. A cylindrical pipe 84 extends axially in a direction away from the ring portion 80. A centrally arranged through-going air canal 86 is provided in the cylindrical pipe 84. The cylindrical pipe 84 comprises a closing surface 89 partly closing the opening 88 (the opening is provided through the air canal 86), since the closing surface 89 is provided with an opening 91.

It is possible to attach a ventilated disc 52 of a type shown in FIG. 5A and FIG. 5B to the ring portion 80. Hereby, it is possible to reduce inconvenient smell and sound originating from the gas released by the stoma.

FIG. 7 illustrates a perspective view of a ventilated cap 90 according to the invention. The ventilated cap 90 comprises a ring-shaped portion 94 internally bordering a dome-shaped portion 92. A grate structure 56 is provided in the dome-shaped portion 92. A filter 54 is arranged under the grate structure 56. The filter 54 may be a carbon filter capable of absorbing components of the gas that is released from the stoma and passes through the filter 54.

Three knobs 38 are provided (evenly distributed) on the top side of the ring-shaped portion 94 of the ventilated cap 90. Each of the knobs 38 are mechanically connected to a rotatably attached attachment element 40 attached to the ring-shaped portion 94.

FIG. 7B illustrates a side view of the ventilated cap 90 shown in FIG. 7A. The ventilated cap 90 comprises a plane, ring-shaped portion 94 provided with knobs 38 each mechanically connected to a corresponding attachment element 40 comprising a distally arranged protrusion 46.

The attachment elements 40 are configured to engage with corresponding mounting holes in an attachment ring as the ones shown in FIG. 3A, FIG. 3B and FIG. 3C.

The ventilated cap 90 comprises a dome-shaped portion 92. A filter 54 is provided in the upper region of the dome-shaped portion 92.

The ventilated cap 90 further comprises an axially extending tubular portion 62 provided with a number of recesses 64. The recesses 64 ease the engagement of the tubular portion 62 with a structure such as a ventilated disc as the ones shown in FIG. 5A and FIG. 5B. The ventilated disc can be attached to the tubular portion 62 by inserting the ventilated disc axially into the inside of the tubular portion 62. Hereby, the gas from the stoma has to pass through two filtering structures. Accordingly, a more efficient filtering of inconvenient smell is achieved. Moreover, sounds generated when evacuating gas through the stoma can be more effectively muffled.

FIG. 7C illustrates a schematic view of the ventilated cap 90 shown in FIG. 7B. The ventilated cap 90 is a plug cap comprising a filtering material 96 centrally arranged in the dome-shaped portion 92. The filtering material 96 can be provided in this position by attaching a ventilated disc (as shown in FIG. 5A and FIG. 5B) with the filtering material 96 centrally in the dome-shaped portion 92. The attachment may be accomplished by introducing the ventilated disc axially along the inner side of the tubular portion 62.

FIG. 7C illustrates a closed cap mounted with an "opposite plug cap" 90, wherein an air permeable member (a bag) is attached (glued) around a centrally arranged hole. The inner "dome space" is filled up with an absorbing material configured to absorb body produced liquid released through the stoma.

The cap 90 has been pressed into the tubular ring 62 by means of the recess 64. The cap 90 is configured to plug the stoma.

FIG. 7D illustrates a schematic view of a ventilated cap 90 in a configuration that almost corresponds to the one shown in FIG. 7C. The ventilated cap 90 illustrated in FIG. 7D comprises a plug member 78 corresponding to the one shown in FIG. 6D. The plug member 78 is attached to the bottom side of a ventilated disc 52 as illustrated in FIG. 5A and FIG. 5B.

The ventilated cap 90 can be applied to colostomies if the stoma has a size that requires a geometric plugging. The plug member 78 is shaped as a foam tube 84. An air-tight attachment plate is attached to the tube 84. The air in the foam tube 84 is guided to the foam material arranged at the attachment point on the tube 84. The function is to retain air and faeces. It is possible to vary the radius of curvature of the cap 90 in order to achieve the desired depth of the cap 90.

FIG. 8 illustrates a perspective view of a ventilated cap 90 that basically corresponds to the one shown in FIG. 7A and FIG. 7B. FIG. 8A illustrates a perspective bottom view. The ventilated cap 90 comprises a flat ring-shaped portion 94 provided with three attachment elements 40 each provided with a distally extending protrusion 46. The three attachment elements 40 are configured to be attached to corresponding mounting holes 36 provided in the attachment ring 4 of the type shown in FIG. 3A and FIG. 3B.

The ventilated cap 90 comprises a tubular portion 62, into which it is possible to provide recesses as shown in FIG. 7B, FIG. 7C and FIG. 7D. The ventilated cap 90 comprises a dome-shaped portion 92 provided with a filter 54.

FIG. 8B illustrates a bottom view of ventilated cap 90 corresponding to the one shown in FIG. 8A. A filter material 96 is attached to the central portion of the ventilated cap 90. The filter material 96 may be attached to a filter plate configured to be axially inserted into the inner side of a tubular portion 62. The attachment elements 40 are configured to engage corresponding mounting holes, e.g. provided in an attachment ring as shown in FIG. 3A and FIG. 3B. The attachment elements 40 comprise distal extending protrusions 46.

FIG. 8C illustrates an open cap 98 according to the invention. The open cap 98 comprises a tubular portion 102 provided with an opening 100. The tubular portion 102 is attached to a flat and circular ring-shaped portion 94. Three knobs 38 are provided along the periphery of the ring-shaped portion 94. The knobs 38 are evenly distributed and rotatably attached to the ring-shaped portion 94.

Each of the knobs 38 is mechanically attached to a corresponding attachment element 40. A tube (e.g. a tube as the one shown in FIG. 2C) may be attached to the open cap 98 in such a manner that the stomi can be emptied through the open cap 98.

FIG. 9A illustrates a ventilated cap 60 provided with a plug member 78. The ventilated cap 60 corresponds to the one shown in FIG. 6D. It can be seen that a plug member 78 is attached to the ventilated cap 60.

FIG. 9B illustrates the plug cap that is attached to the ventilated cap 60 shown in FIG. 9A. The plug cap is intended for an ileostomy and comprises a filter material 96 provided on the central portion of the bowl-shaped portion 82. The plug cap comprises a ring portion 80.

FIG. 9C illustrates a schematic view of a pipe 84 configured to be attached to the plug cap shown in FIG. 9B. The pipe 84 may preferably be produced in polyurethane (PU). The pipe 84 may preferably be covered with a plastic layer that is impermeable to water. A centrally arranged longitudinal air canal 86 is provided in the pipe 84.

Figure 10:
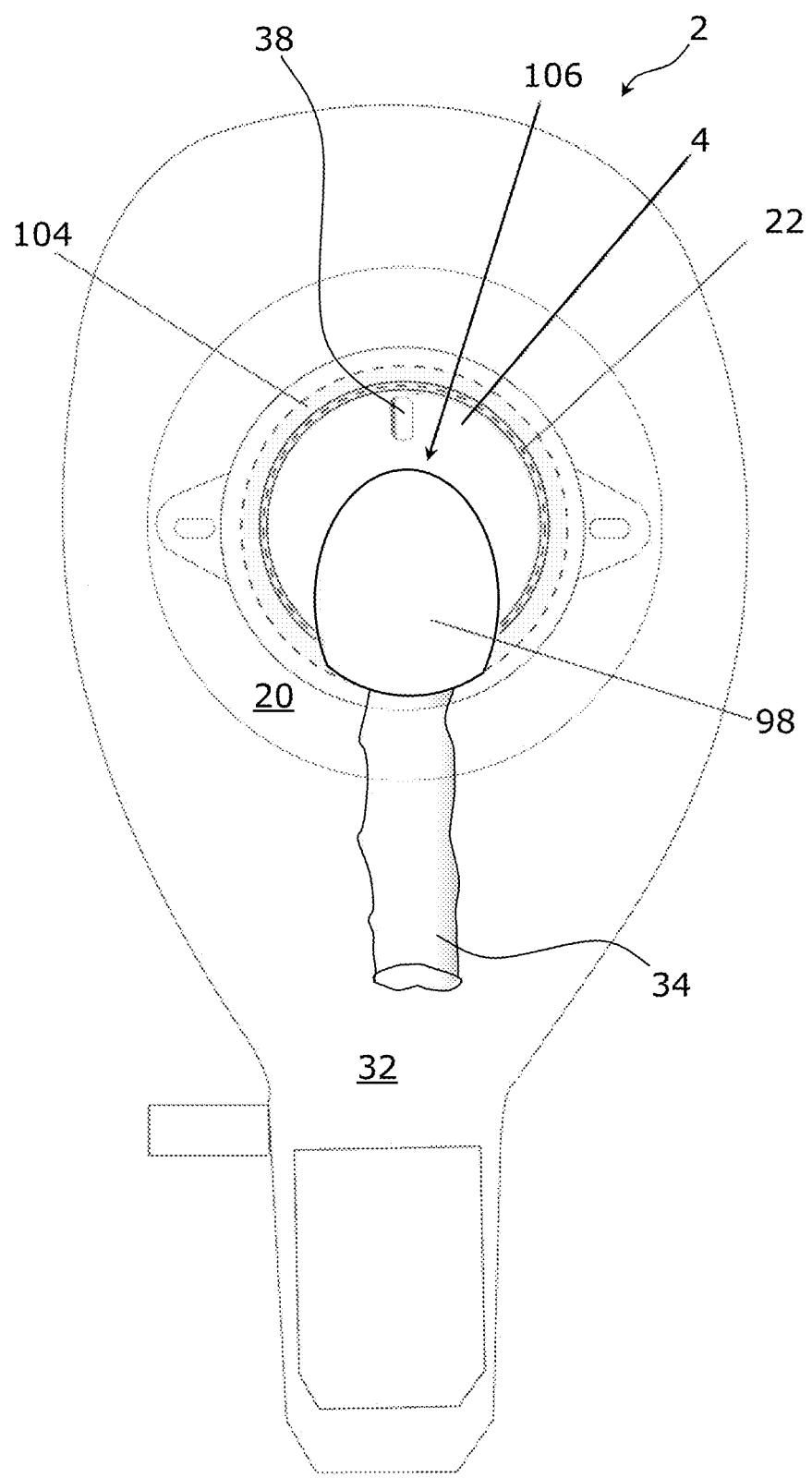
FIG. 10 shows an ostomy device according to the invention.

FIG. 10 illustrates an ostomy device 2 according to the invention. The ostomy device 2 comprises an open cap 98 and a latex tube 34 attached thereto. The latex tube 34 is provided in a conventional ostomy bag 32.

A base plate 20 is attached to the skin surrounding a stoma. An attachment ring 4 is mechanically attached to the base plate 20. The attachment ring 4 is attached to the flange 22 on the coupling ring 104 of the base plate 20. The attachment ring 4 comprises a knob 38 (there may be more than one knob 38, e.g. three knobs 38).

The open cap 98 has a closed end 106 facing upwards towards the knob 38 shown. On the contrary, the opening 106 is oriented in the opposite direction, in which the tube 34 extends. The open cap 98 can easily be dismounted and be replaced by e.g. a closed cap or a ventilated cap provided with a plug member.

FIG. 11A illustrates a closing disc 42 according to the invention provided with knobs 38 and an inner thread 112 configured to receive a closure member 114 provided with a corresponding outer thread 110 and two protrusion structures 116 arranged at the top side of the closure member 114. The closure member 114 may preferably be provided with a filter member configured to muffle the sound generated (when evacuating gas through the stoma) and neutralise foul smell (from gas released through the stoma). Hereby, the degree of closure of the stoma may be regulated by rotating the closure member 114. Rotation of the closure member 114 will displace the closure member 114 axially and hereby either press further against the stoma or reduce the pressure against the stoma dependent on the rotational direction. Accordingly, the closure member 114 makes it possible to regulate the degree of closure of the stoma.

FIG. 11B illustrates a ventilated cap 60 according to the invention. The ventilated cap is provided with three knobs 38. One of the knobs 38 is indicated with hatching. A small gap 120 is provided under the knobs 38 in order to ease the dismounting of the ventilated cap 60. The ventilated cap 60 can be lifted by means of a fingernail 122 and hereby be dismounted from an attachment ring as indicated.

FIG. 11C illustrates a close-up view of the ventilated cap shown in FIG. 11B. It can be seen that that a gap 120 is provided under the distal portion of the knob 38 and that the gab 120 is configured to receive the top portion of a fingernail 122.

FIG. 11D illustrates a cylindrical member 118 according to the invention. The cylindrical member 118 is intended to be used with a "low" stoma (wherein the stoma is arranged in or just below the "stomach level") since the stoma is not capable of guiding the body fluids away from the base plate. Normally, the body fluids will be brought into contact with the skin and gradually decompose the adhesive of the base plate. By arranging a threaded cylindrical member 118 on a closing disc, it is possible to bring the cylindrical member 118 as far as required towards the stoma until the cylindrical member 188 presses the stoma upwards through the opening provided in the cylindrical member 118. Accordingly, the body fluids will be no longer be brought into contact with the skin. The body fluids will be guided through the cylindrical member 118 into the ostomy bag.

LIST OF REFERENCE NUMERALS

2 Ostomy device
4 Attachment ring
5 Opening
6 Connection element (connection ring)
8 Attachment profile (narrow edge)
10 Attachment bending
12 Opening
14 Exposed area
16 Stoma
18 Faeces
20 Base plate
22 Flange
24 Locking recess
26 Coupling ring
28 Attachment recess
30 Skin
32 Ostomy bag
34 Tube (latex tube)
36 Mounting hole
38 Knob
40 Attachment element
42 Closing disc (cover)
44, 46 Protrusion
47 Convex portion
48 Tubular portion
50 Concave contact surface
I, II Section line
$H_1$, $H_2$, $H_3$ Height
52 Ventilated disc (cover)
54 Filter
56 Grate structure
57 Disc-formed portion
58 Inner wall
59 Ring-shaped portion
60 Ventilated cap
62 Tubular portion
64 Recess
66, 66' Closing ring
68 Recess
70 Flange
72 Contact wall
74 Protrusion
76 Tapered ring structure
78 Plug member
80 Ring portion
82 Bowl-shaped portion
84 Pipe (e.g. a foam pipe)
86 Air canal
88 Opening
89 Closing surface
90 Ventilated cap
91 Opening
92 Dome-shaped portion
94 Ring-shaped portion
96 Filter material
98 Open cap
100 Opening
102 Pipe portion
104 Coupling ring
106 Closed end
108 Disc
110, 112 Threaded portion
114 Closure member
116 Protrusion structure
118 Cylindrical member
120 Gap
122 Fingernail
X Longitudinal axis

The invention claimed is:

1. A device for attachment to an ostomy base plate comprising:
   (a) an attachment ring comprising;
     (i) a circular opening;
     (ii) distal attachment structures on a ring portion; and
     (iii) a proximal attachment profile shaped as a ring-shaped disc arranged on the periphery of the attachment ring with proximal attachment structures that are configured to be detachably attached to attachment elements on a distal side of the base plate; and (b) a connection element as a connection ring comprising: additional structures configured to be detachably attached to the attachment structures of the attachment ring.

2. The device of claim 1 further comprising a closing disc, wherein the closing disc comprises a structure configured to mount a tube, wherein the closing disc is configured to be detachably attached to the attachment ring.

3. The device of claim 1 further comprising a ventilated cap configured to be detachably attached to the attachment ring.

4. The device of claim 3 wherein the ventilated cap comprises structures configured to be detachably attached to the attachment ring.

5. The device of claim 3 wherein the ventilated cap comprises a filter integrated in the ventilated cap.

6. The device of claim 1 further comprising one or more rotatable knobs provided on the top side of one of the additional structures, wherein each rotatable knob is configured to lockingly engage a corresponding structure.

7. The device of claim 1 wherein each of the additional structures are provided with one or more recesses configured to engagingly receive one or more attachment elements and/or protrusions, wherein each of the additional structures is configured to be axially locked by rotating the additional structure in such a manner that the one or more attachment elements and/or protrusions are displaced with respect to the recesses.

8. The device of claim 1 further comprising a plug member comprising a ring portion constituting the upper periphery of the plug member, wherein a bowl-shaped portion extends under the ring portion, wherein a centrally arranged opening is provided in the bowl-shaped portion, wherein the ostomy device comprises a pipe having a through-going air canal, wherein the pipe is configured to be inserted into a stoma, wherein the pipe is configured to evacuate gas from the stoma through the opening.

9. The device of claim 1 further comprising a closing ring comprising a cylindrical contact wall, wherein a flange is provided in the proximal end of the cylindrical contact wall, wherein a tapered ring structure is provided in the proximal end of the contact wall, and wherein a centrally arranged opening is provided in the closing ring.

10. The device of claim 1 further comprising an open cap, wherein the open cap comprises a pipe portion provided with an opening.

11. The device of claim 6 wherein a gap is provided under at least a portion of at least one of the rotatable knobs, wherein the gap is configured to receive the top portion of a fingernail.

12. The device of claim 2 wherein the closing disc comprises a cylindrical portion arranged centrally and extending axially and coaxially with respect to a ring-shaped outer part surrounding the centrally arranged cylindrical portion.

13. The device of claim 2 wherein the closing disc is provided with an inner thread configured to receive a corresponding member provided with a corresponding outer thread.

14. The device of claim 13 further comprising a cylindrical member provided with an outer thread adapted to fit the inner thread of the closing disc.

15. A device for attachment to an ostomy base plate, wherein the device comprises:
(a) a ventilated disc comprising:
   (i) a disc comprising a peripheral ring shaped portion;
   (ii) a disc-formed portion arranged inside the ring-shaped portion and comprising a central grate structure;
   (iii) proximal attachment elements provided on the proximal side of the ventilated disc configured to be detachably attached to a locking flange of the base plate; and
   (iv) distal attachment structures; and
(b) a connection element as a connection ring comprising additional structures configured to be detachably attached to the distal attachment structures of the ventilated disc; and
(c) a filter adjacent to the central grate structure of the disc-formed portion and configured to retain gas components released from a stoma.

* * * * *